United States Patent
Yamakita

(10) Patent No.: US 7,864,921 B2
(45) Date of Patent: Jan. 4, 2011

(54) RADIATION IMAGE DETECTING APPARATUS

(75) Inventor: Hiroshi Yamakita, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 129 days.

(21) Appl. No.: 12/394,577

(22) Filed: Feb. 27, 2009

(65) Prior Publication Data
US 2009/0224188 A1  Sep. 10, 2009

(30) Foreign Application Priority Data
Feb. 28, 2008 (JP) ............................. 2008-047252

(51) Int. Cl.
*G01N 23/04* (2006.01)
(52) U.S. Cl. .................... 378/62; 378/37; 378/155
(58) Field of Classification Search ............ 378/37, 378/62, 101, 108–112, 154–160
See application file for complete search history.

(56) References Cited

U.S. PATENT DOCUMENTS
7,039,151 B2  5/2006  Tsujii ........................... 378/7

*Primary Examiner*—Courtney Thomas
(74) *Attorney, Agent, or Firm*—Sughrue Mion, PLLC

(57) ABSTRACT

Radiation images, which are obtained while reciprocally moving a scattered radiation removing means, are efficiently corrected. An image processing apparatus performs shading correction and gain correction on a radiation image which is obtained by detecting radiation that passes through a subject and is detected by a radiation detector while reciprocally moving the scattered radiation removing means, using a reference image. An irradiation control means controls irradiation of radiation during obtainment of the reference image such that irradiation is ceased after the scattered radiation removing means is reciprocally moved for k periodic reciprocal motions (k is an integer greater than or equal to 1) from initiation of irradiation. Meanwhile, irradiation of the radiation during obtainment of the radiation image is controlled such that irradiation is ceased after the scattered radiation removing means is reciprocally moved for m periodic reciprocal motions (m is an integer greater than or equal to 1).

6 Claims, 4 Drawing Sheets

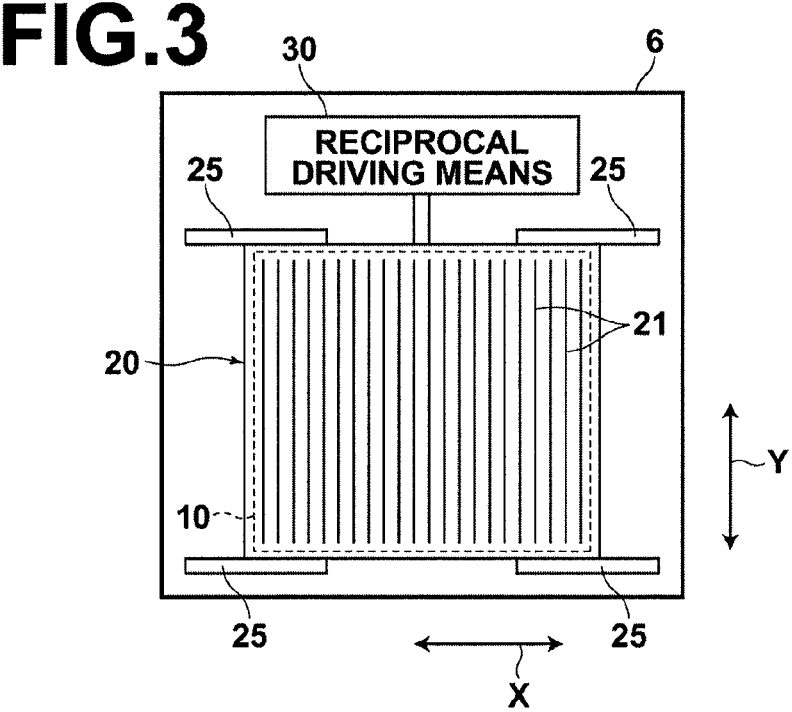
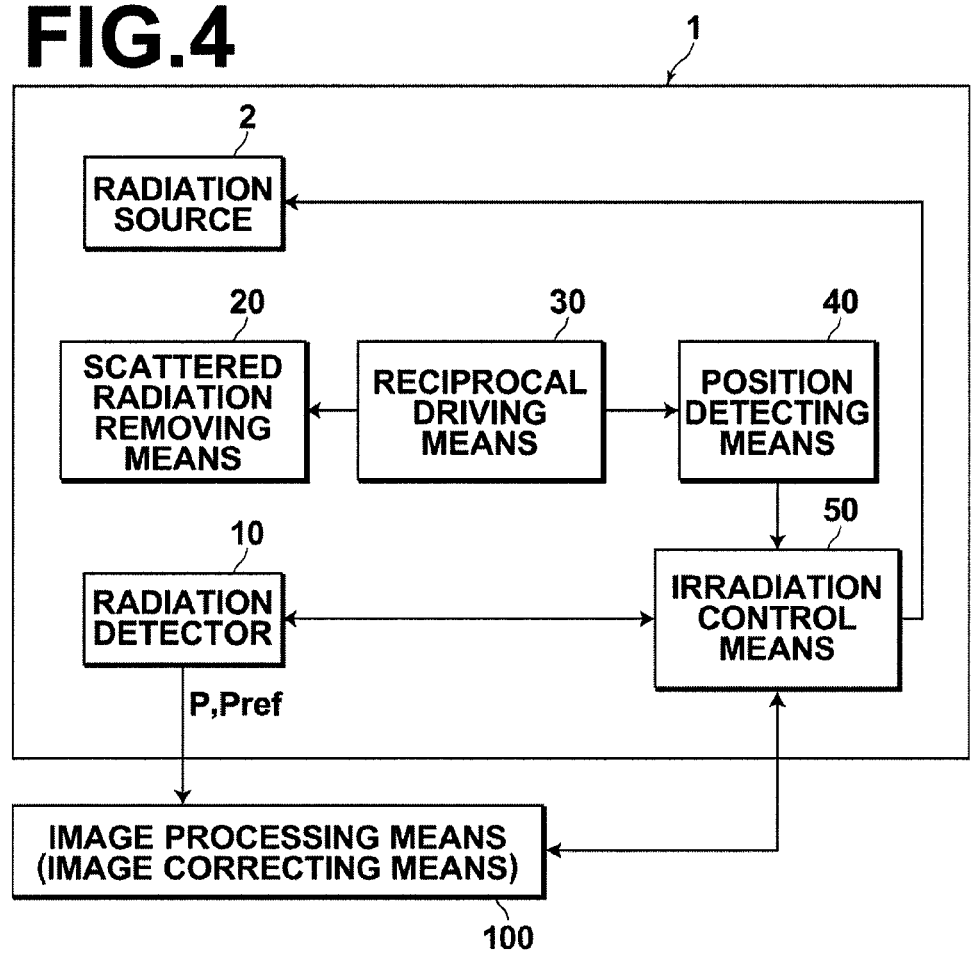

RADIATION IMAGE DETECTING APPARATUS

BACKGROUND OF THE INVENTION

1. Field of the Invention

The present invention is related to a radiation image detecting apparatus that obtains radiation images while moving a scattered radiation removing means on a radiation detector.

2. Description of the Related Art

Various types of radiation image detectors that generate charges by being irradiated with radiation which has passed through subjects and record radiation images of the subjects by accumulating the charges have been proposed and are in actual use in the field of medicine and the like. For example, there are radiation detectors that utilize amorphous selenium, which generates electrical charges when irradiated by radiation. In radiation image processing apparatuses, scattered radiation removing means (grids), constituted by a plurality of lead plates which are arranged parallel to each other, are provided between radiation sources that emit radiation and the radiation image detectors. This configuration enables scattered components of radiation to be removed by the scattered radiation removing means.

When radiation images are obtained with the aforementioned scattered radiation removing means in a static state, periodic stripes (lattice stripes) appear within the radiation images due to the scattered radiation removing means. A method for preventing generation of the periodic stripes, by reciprocally moving the scattered radiation removing means in the horizontal direction has been proposed (refer to U.S. Pat. No. 7,039,151, for example).

In the case that the scattered radiation removing means is reciprocally moved as proposed in U.S. Pat. No. 7,039,151, the periodic stripes caused by the scattered radiation removing means can be reduced. However, noise components due to the scattered radiation removing means are generated as irregularities in the low frequency components of radiation images. Therefore, administering shading correction or gain correction onto radiation images, which are obtained by imaging subjects, using a reference image, which has been obtained in advance, may be considered.

However, noise components appear in different manners among radiation images, which are obtained by irradiating radiation onto radiation detectors for different amounts of time while the scattered radiation removing means is being reciprocally moved. Therefore, if shading correction or gain correction is administered onto such radiation images using a single reference image, there is a problem that residual error irregularities are generated. On the other hand, preparing a plurality of reference images, which are obtained by irradiating radiation onto radiation detectors for different amounts of time, may be considered. In this case, a reference image onto which radiation was irradiated for the same amount of time as a radiation image to be corrected may be selected as the reference image to be used for correction. However, there is a problem that this method is inefficient when performing shading correction.

SUMMARY OF THE INVENTION

The present invention has been developed in view of the foregoing circumstances. It is an object of the present invention to provide a radiation image detecting apparatus which is capable of efficiently correcting radiation images which are obtained while reciprocally moving scattered radiation removing means, while preventing the generation of residual error irregularities.

A first radiation image detecting apparatus of the present invention is equipped with:

a radiation source for irradiating radiation;

a radiation detector for detecting radiation, which is irradiated by the radiation source onto a subject and which has passed through the subject, as a radiation image;

scattered radiation removing means for removing scattered components of the radiation, provided on the radiation detector toward the side onto which the radiation is irradiated;

reciprocal drive means, for reciprocally moving the scattered radiation removing means in one of a main direction and a sub direction of the radiation detector;

image correcting means, for correcting the radiation image which is obtained by the radiation detector by detecting the radiation which has passed through the subject with a reference image; and irradiation control means, for controlling the irradiation of radiation onto the radiation detector; and is characterized by:

the irradiation control means controlling irradiation of the radiation during obtainment of the reference image such that the irradiation is ceased after the scattered radiation removing means is reciprocally moved for k periodic reciprocal motions (k is an integer greater than or equal to 1) from initiation of the irradiation, and controlling irradiation of the radiation during obtainment of the radiation image such that the irradiation is ceased after the scattered radiation removing means is reciprocally moved for m periodic reciprocal motions (m is an integer greater than or equal to 1).

Here, the irradiation control means only needs to cease the irradiation of radiation after the scattered radiation removing means is reciprocally moved for k periodic reciprocal motions, regardless of the position of the scattered radiation removing means at the time when irradiation is initiated. The parameters k and m need only to be integers, and either k=m or k≠m are possible. In addition, the irradiation control means may set the value of m to be the smallest integer which is not less than a value n (n=a/(Imax·Tm), wherein Imax is the maximum bulb current of the radiation source, Tm is the amount of time for reciprocal motion of the scattered radiation removing means, and a is the mAs value of radiation).

A second radiation image detecting apparatus is equipped with:

a radiation source for irradiating radiation;

a radiation detector for detecting radiation, which is irradiated by the radiation source onto a subject and which has passed through the subject, as a radiation image;

scattered radiation removing means for removing scattered components of the radiation, provided on the radiation detector toward the side onto which the radiation is irradiated;

reciprocal drive means, for reciprocally moving the scattered radiation removing means in one of a main direction and a sub direction of the radiation detector;

position detecting means, for detecting the position of the scattered radiation removing means with respect to the radiation detector;

image correcting means, for correcting the radiation image which is obtained by the radiation detector by detecting the radiation which has passed through the subject with a reference image; and irradiation control means, for controlling the timing of irradiation of radiation onto the radiation detector based on the position of the scattered radiation removing means detected by the position detecting means when obtaining the radiation image and the reference image; and is characterized by the irradiation control means controlling irradiation of the radiation during obtainment of the reference image such that the irradiation is initiated when the scattered radiation removing means is at its maximally displaced position within the reciprocal motion thereof, and is ceased when the scattered radiation removing means is reciprocally moved for p/2 periodic reciprocal motions (p is an integer greater than or equal to 1), and controlling irradiation of the radiation during obtainment of the radiation image such that the irradiation is initiated when the scattered radiation removing means is at its maximally displaced position within the reciprocal motion thereof, and is ceased when the scattered radiation removing means is reciprocally moved for q/2 periodic reciprocal motions (p is an integer greater than or equal to 1).

Here, the "radiation image" refers to any image which is obtained by detecting radiation which has been irradiated onto subjects. Examples of such an image include: radiation images obtained by a mammography apparatus; and radiation images obtained by imaging the chests of subjects. The "radiation images" are not limited to those for medical use, and may also include radiation images which are employed for non destructive inspections. The "reference image" is an image that serves as a reference when administering shading correction or gain correction, and is a uniform image (a so-called plain image) obtained by imaging in a state without a subject, for example.

The position detecting means may detect the position of the scattered radiation removing means with respect to the radiation detector by any method. The position of the scattered radiation removing means may be detected from the reciprocal driving means, for example, or by known techniques, such as by an optical means.

The irradiation control means initiates irradiation of the radiation when the scattered radiation removing means is at its maximally displaced position, and ceases the irradiation when the scattered radiation removing means has moved reciprocally for q/2 periodic reciprocal motions (wherein q is an integer greater than or equal to 1). As a result, the irradiation start timing and the irradiation end timing both occur when the scattered radiation removing means is at its maximally displaced position. The parameters p and q need only to be integers, and either p=q or p≠q are possible. In addition, the irradiation control means may set the value of q to be the smallest integer which is not less than a value r (r=a/(Imax·tm), wherein Imax is the maximum bulb current of the radiation source, tm is the amount of time for the scattered radiation removing means to move one way in the reciprocal motion thereof, and a is the mAs value of radiation).

Here, in the case that the formula a/(Imax·Tm) or the formula a/(Imax·tm) yields a value having decimal places, the integers m and q may be calculated by rounding up, rounding down, or rounding off the decimal places. Rounding up is preferred, because causing current that exceeds the maximum bulb current to flow affects the radiation source. In addition, the correction of the radiation image using the reference image may be shading correction or gain correction.

The first radiation image detecting apparatus of the present invention is equipped with: the radiation source for irradiating radiation; the radiation detector for detecting radiation, which is irradiated by the radiation source onto a subject and which has passed through the subject, as a radiation image; the scattered radiation removing means for removing scattered components of the radiation, provided on the radiation detector toward the side onto which the radiation is irradiated; the reciprocal drive means, for reciprocally moving the scattered radiation removing means in one of a main direction and a sub direction of the radiation detector; the image correcting means, for correcting the radiation image which is obtained by the radiation detector by detecting the radiation which has passed through the subject with a reference image; and the irradiation control means, for controlling the irradiation of radiation onto the radiation detector. The irradiation control means controls irradiation of the radiation during obtainment of the reference image such that the irradiation is ceased after the scattered radiation removing means is reciprocally moved for k periodic reciprocal motions (k is an integer greater than or equal to 1) from initiation of the irradiation, and controls irradiation of the radiation during obtainment of the radiation image such that the irradiation is ceased after the scattered radiation removing means is reciprocally moved for m periodic reciprocal motions (m is an integer greater than or equal to 1). In cases that the amount of time that radiation is irradiated when obtaining a reference image and the amount of time that radiation is irradiated when obtaining a radiation image are integer multiples of the periods of reciprocal motion of the scattered radiation removing means, noise components which are included in the reference image and the radiation image are substantially the same. Therefore, if a single reference image is obtained, the reference image may be used to correct radiation images which are obtained by being irradiated with radiation for different amounts of time. Accordingly, residual error irregularities can be reduced, and radiation images can be corrected efficiently.

Note that the irradiation control means may set the value of m to be the smallest integer which is not less than a value n (n=a/(Imax·Tm), wherein Imax is the maximum bulb current of the radiation source, Tm is the amount of time for reciprocal motion of the scattered radiation removing means, and a is the mAs value of radiation). In this case, the irradiation of radiation can be controlled within the range of the maximum bulb current, without changing the speed at which the scattered radiation removing means is moved reciprocally.

The second radiation image detecting apparatus is equipped with: the radiation source for irradiating radiation; the radiation detector for detecting radiation, which is irradiated by the radiation source onto a subject and which has passed through the subject, as a radiation image; the scattered radiation removing means for removing scattered radiation components of the radiation, provided on the radiation detector toward the side onto which the radiation is irradiated; the reciprocal drive means, for reciprocally moving the scattered radiation removing means in one of a main direction and a sub direction of the radiation detector; the position detecting means, for detecting the position of the scattered radiation removing means with respect to the radiation detector; the image correcting means, for correcting the radiation image which is obtained by the radiation detector by detecting the radiation which has passed through the subject with a reference image; and the irradiation control means, for controlling the timing of irradiation of radiation onto the radiation detector based on the position of the scattered radiation removing means detected by the position detecting means when obtaining the radiation image and the reference image. The irradiation control means controls irradiation of the radiation during obtainment of the reference image such that the irradiation is initiated when the scattered radiation removing means is at its maximally displaced position within the reciprocal motion thereof, and is ceased when the scattered radiation removing means is reciprocally moved for p/2 periodic reciprocal motions (p is an integer greater than or equal to 1), and controls irradiation of the radiation during obtainment of the radiation image such that the irradiation is initiated when the scattered radiation removing means is at its maximally displaced position within the reciprocal motion thereof, and is ceased when the scattered radiation removing means is reciprocally moved for q/2 periodic reciprocal motions (p is an integer greater than or equal to 1).

Note that the irradiation control means may set the value of q to be the smallest integer which is not less than a value r (r=a/(Imax·tm), wherein Imax is the maximum bulb current of the radiation source, tm is the amount of time for the scattered radiation removing means to move one way in the reciprocal motion thereof, and a is the mAs value of radiation). In this case, the irradiation of radiation can be controlled within the range of the maximum bulb current, without changing the speed at which the scattered radiation removing means is moved reciprocally.

BRIEF DESCRIPTION OF THE DRAWINGS

FIG. 3 is a plan view of that illustrates the inner structure of the imaging stage of the radiation image detecting apparatus illustrated in FIG. 1.

FIG. 4 is a block diagram that illustrates the radiation image detecting apparatus according to a preferred embodiment of the present invention.

BEST MODE FOR CARRYING OUT THE INVENTION

Figure 1:
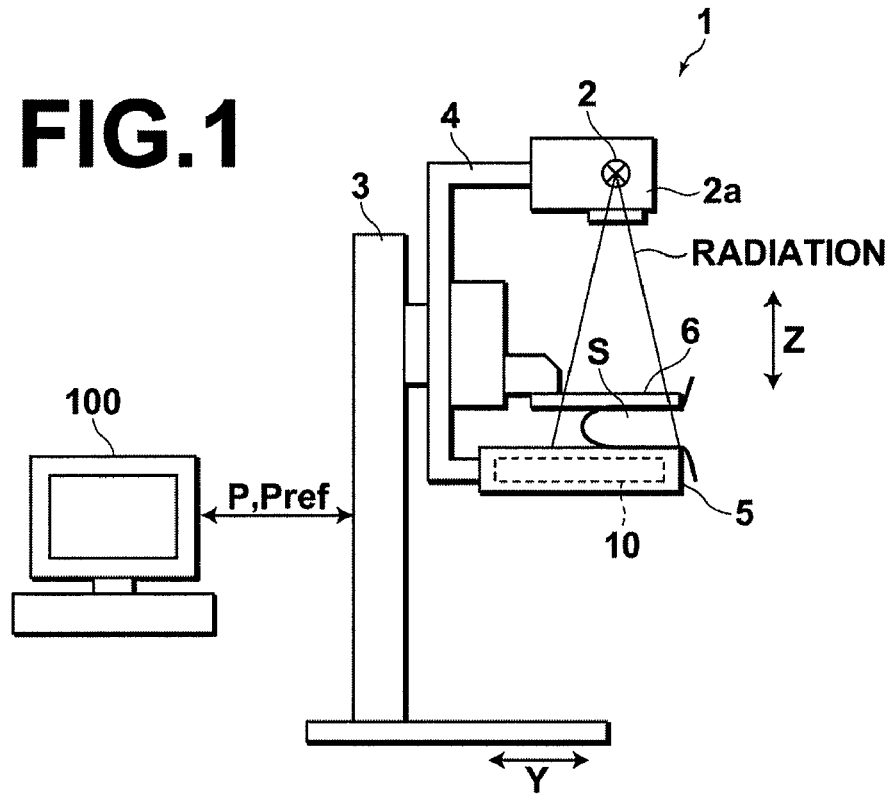
FIG. 1 is a diagram that schematically illustrates a radiation image detecting apparatus, according to a preferred embodiment of the present invention.

Hereinafter, a radiation image detecting apparatus of the present invention will be described with reference to the attached drawings. FIG. 1 is a diagram that schematically illustrates a radiation image detecting apparatus 1 for obtaining radiation images, according to a preferred embodiment of the present invention. The radiation image detecting apparatus 1 of FIG. 1 is a mammography apparatus for obtaining radiation images of breasts, and is equipped with: a radiation source 2; a base 3; a support 4; an imaging stage 5; and a pressing plate 6. The base 3 holds the support 4 such that the support 4 is movable in the direction indicated by arrow Z, according to the position of subjects S. The radiation source 2 emits radiation toward the subjects S, and is housed in a radiation source housing section 2a, which is mounted to the upper portion of the support 4.

The imaging stage 5 houses a radiation detector 10 therein. The radiation detector 10 obtains radiation images P by detecting radiation which is emitted from the radiation source 2 and has passed through the subjects S. The imaging stage 5 is mounted to the lower portion of the support 4 so as to face the radiation source 2. In addition, the pressing plate 6 for pressing the subject S against the imaging stage 5 is provided above the imaging stage 5. The pressing plate 6 is mounted such that it is movable in the direction indicated by arrow Z with respect to the support 4.

The radiation detector 10 accumulates radiation image data constituted by radiation which has passed through the subjects S as electrostatic latent images. The accumulated electrostatic latent images are read out, to detect the transmittance distribution of the radiation as the radiation images. Note that the radiation detector 10 may be of any configuration as long as it detects radiation and outputs the detected radiation as image data. Examples of radiation detectors that may be employed as the radiation detector 10 include TFT type solid state detectors and optical readout type solid state detectors.

An image processing apparatus 100 administers various image processes onto the radiation images P obtained by the radiation detector 10 and displays the radiation images P. Particularly, the image processing apparatus 100 administers functions as an image correcting means that administers shading correction and gain correction on the radiation images P. Here, the image processing apparatus 100 administers the shading correction and gain correction by known techniques, using a reference image Pref, which is obtained by the radiation detector 10 by performing imaging in a state in which there is no subject.

Figure 2:
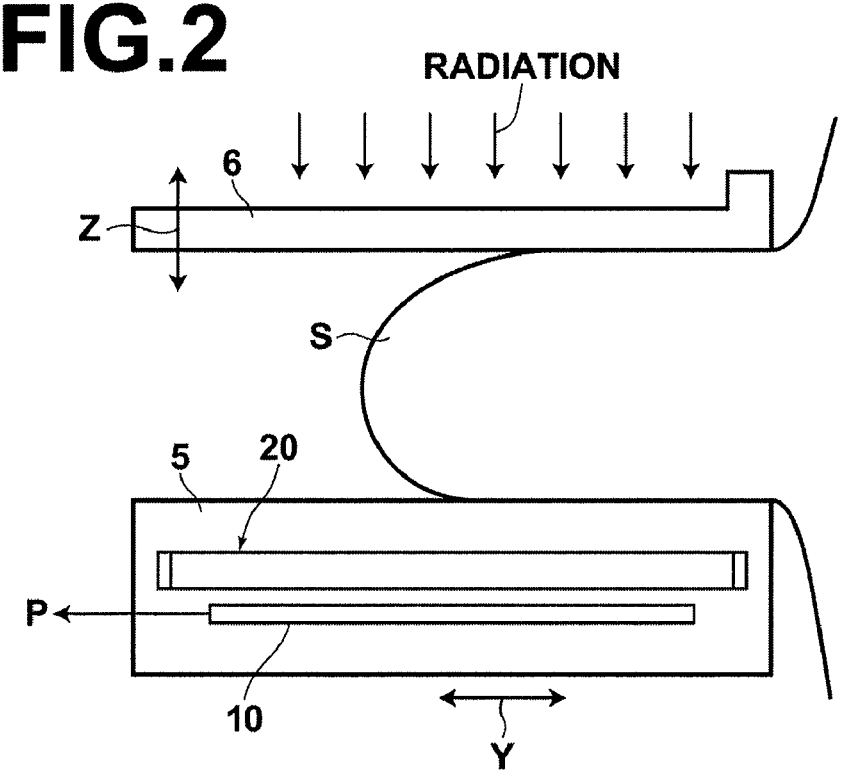
FIG. 2 is a schematic diagram that illustrates the inner structure of an imaging stage of the radiation image detecting apparatus illustrated in FIG. 1.

FIG. 2 is a schematic diagram that illustrates the inner structure of the imaging stage 5 of FIG. 1. FIG. 3 is a plan view of the imaging stage 5. A scattered radiation removing means 20 is provided within the imaging stage 5 such that it is positioned between the radiation source 2 and the radiation detector 10. The scattered radiation removing means 20 is of a configuration in which a plurality of plates 21 made of lead or the like are arranged parallel to each other at predetermined intervals (approximately 0.3 mm, for example) such that they point toward the radiation source (focal point). The scattered radiation removing means 20 transmits non scattered components of radiation and absorbs (removes) scattered radiation components with the plates 21.

Note that FIG. 3 illustrates an example in which the plates 21 of the scattered radiation removing means 20 are provided such that the longitudinal directions thereof are parallel to the sub direction of the radiation detector 10 (indicated by arrow Y). Alternatively, the plates 21 may be provided in both the main direction (indicated by arrow X) and the sub direction (indicated by arrow Y) to form a lattice. As a further alternative, the plates 21 may be provided such that the longitudinal directions thereof are inclined with respect to the main direction (indicated by arrow X) and the sub direction (indicated by arrow Y) of the radiation detector 10.

A reciprocal driving means 30 that moves the scattered radiation removing means 20 reciprocally with respect to the radiation detector 10 is attached to the scattered radiation removing means 20 (grid 20). The reciprocal driving means 30 is constituted by a mechanism that converts the rotation of a motor into reciprocal motion, for example. The reciprocal driving means 30 moves the scattered radiation removing means 20 reciprocally in a direction perpendicular to the longitudinal direction of the plates 21 of the scattered radiation removing means 20 (indicated by arrow Y) at a constant speed. Accordingly, the position of the scattered radiation removing means 20 changes periodically with respect to the radiation detector 10 with the passage of time (refer to FIG. 5, to be described later).

FIG. 4 is a block diagram that illustrates the configuration of the radiation image detecting apparatus 1 according to the preferred embodiment of the present invention, of FIG. 1. As illustrated in FIG. 4, the radiation image detecting apparatus 1 is further equipped with: a position detecting means 40; and an irradiation control means 50. The position detecting means 40 is constituted by an encoder which is mounted to the rotating axis of the motor of the aforementioned reciprocal driving means 30, for example, and functions to detect the position of the scattered radiation removing means 20.

Figure 5:
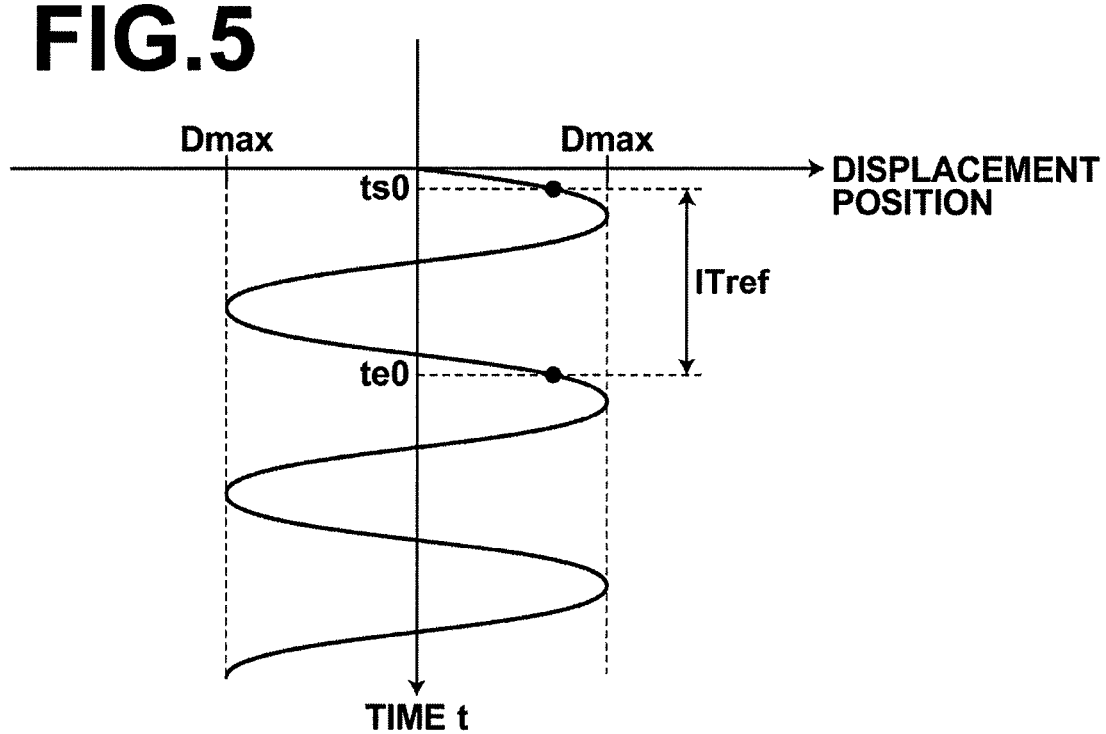
FIG. 5 is a graph that illustrates an example of the relationship between irradiation timings and movement of a scattered radiation removing means when the radiation image detecting apparatus of FIG. 4 obtains a reference image.
Figure 6:
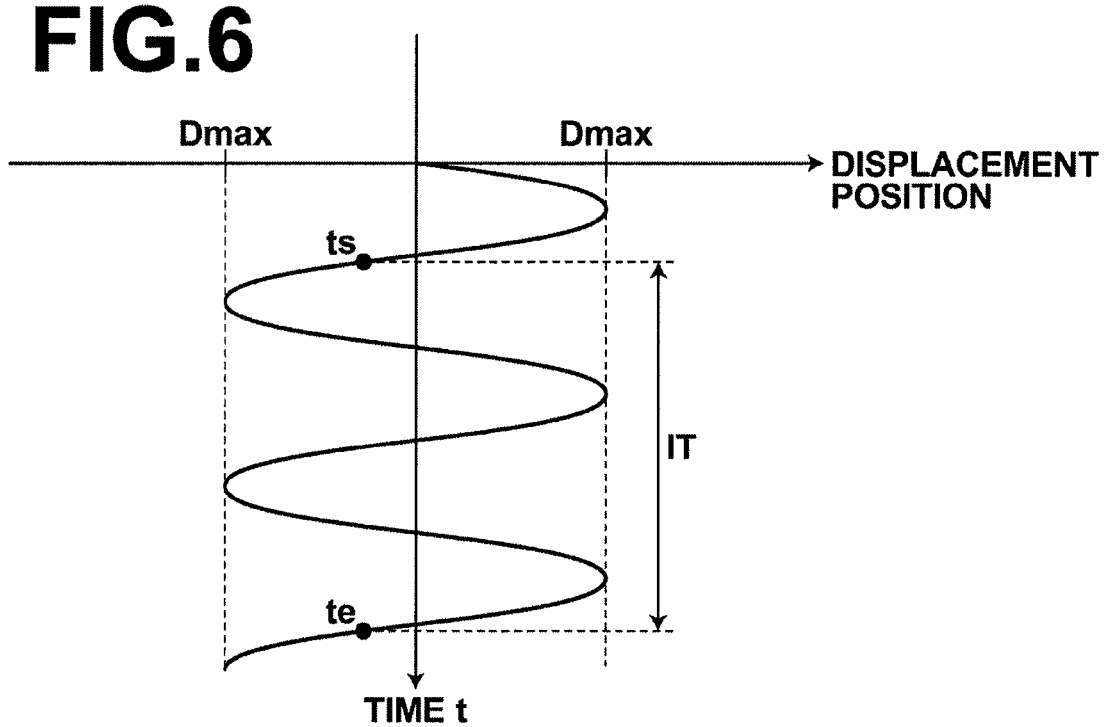
FIG. 6 is a graph that illustrates an example of the relationship between irradiation timings and movement of a scattered radiation removing means when the radiation image detecting apparatus of FIG. 4 obtains a radiation image.

The irradiation control means 50 controls the amounts of time and the timings of irradiation of radiation detected by the position detecting means 40 when obtaining the radiation images P, which is obtained by the radiation detector 10 detecting radiation which has passed through subjects, and the reference image Pref, which is employed by the image processing apparatus 100 (image correcting means 100) to administer corrections onto the radiation images P, based on the position of the scattered radiation removing means 20. Specifically, FIG. 5 is a graph that illustrates an example of the relationships among an irradiation start timing, an irradiation end timing, and movement of the scattered radiation removing means 20 when obtaining a reference image Pref. FIG. 6 is a graph that illustrates an example of the relationships among an irradiation start timing, an irradiation end timing, and movement of the scattered radiation removing means 20 when obtaining a radiation image P. The control of irradiation timings will be described with reference to FIG. 5 and FIG. 6.

First, when obtaining the reference image Pref, the irradiation control means 50 exerts control such that radiation is irradiated from the radiation source 2 at an irradiation start timing ts0, as illustrated in FIG. 5. At this time, the irradiation control means 50 stores the position of the scattered radiation removing means 20, which is detected by the position detecting means 40, or the time at the irradiation start timing ts0. Here, the scattered radiation removing means 20 may be at any position at the irradiation start timing ts0, and the irradiation control means 50 may initiate irradiation as soon as an irradiation initiation command is input, and preparations are complete.

The irradiation control means 50 exerts control such that the irradiation of radiation is ceased, when it is detected that the scattered radiation removing means 20 has moved for k periodic reciprocal motions (k is an integer greater than or equal to 1) after initiation of the irradiation. The number of periodic reciprocal motions may be detected by the position detecting means 40. Alternatively, the amount of time for one periodic reciprocal motion may be measured in advance, and the number of periodic reciprocal motions may be calculated from the elapsed time from the initiation of the irradiation. At this time, k may be any integer which is greater than or equal to 1. FIG. 5 illustrates an example of a reference image Pref, which is obtained by irradiating radiation for an amount of time ITref that corresponds to a single periodic reciprocal motion (k=1). In addition, the integer k may be set in the irradiation control means 50 in advance, or may be set by an operator.

On the other hand, when obtaining a radiation image P, the irradiation control means 50 exerts control such that radiation is irradiated from the radiation source 2 at an irradiation start timing ts, as illustrated in FIG. 6. At this time, the irradiation control means 50 stores the position of the scattered radiation removing means 20, which is detected by the position detecting means 40 at the irradiation start timing ts0. Here, no particular control with regard to the relationship between the irradiation start timing and the position of the scattered radiation removing means 20 is necessary. Further, it is not necessary for the irradiation start timing ts to be the same as the irradiation start timing ts0, which is employed when obtaining the reference image Pref. Accordingly, the irradiation control means 50 may initiate irradiation as soon as preparations are complete.

The irradiation control means 50 exerts control such that the irradiation of radiation is ceased, when it is detected that the scattered radiation removing means 20 has moved for m periodic reciprocal motions (m is an integer greater than or equal to 1) after initiation of the irradiation. Note that m may be any integer which is greater than or equal to 1. FIG. 6 illustrates an example of a radiation image P, which is obtained by irradiating radiation for an amount of time IT that corresponds to a two periodic reciprocal motions (m=2).

Here, the amount of irradiation time (the integer m) when obtaining the radiation image P may be determined by operator input to the irradiation control means 50. Alternatively, the amount of irradiation time may be determined in the following manner. When an mAs value of radiation necessary to obtain a radiation image P is specified (the mAs value is specified by balancing out the desire to reduce the radiation dosage irradiated onto a subject and the desire to ensure favorable image quality), the irradiation control means 50 calculates the value of the integer m according to the following two formulas (1) and (2):

$$m = \text{the smallest integer not less than a value } n \quad (1)$$

$$n = a/(I_{max} \cdot T_m) \quad (2)$$

wherein Imax is the maximum bulb current of the radiation source, Tm is the amount of time for reciprocal motion of the scattered radiation removing means 20, and a is the mAs value of radiation.

In the case that the number n calculated by Formula (2) includes decimal places, the decimal places are rounded up, then the value of the integer m is calculated (by Formula (1)). For example, consider a case that the maximum bulb current Imax of the radiation source 2 is 20 mA, and the amount of time Tm for reciprocal motion of the scattered radiation removing means 20 is 1.6 seconds. In this case, if a radiation image P is to be obtained with an mAs value of a=90 mAs, the irradiation control means 50 calculates n=a/(Imax·Tm)= 2.8125, and derives n=3 by rounding up the decimal places. Accordingly, the irradiation control means 50 exerts control such that irradiation is ceased at a timing te, which is after three periodic reciprocal motions (m=3) from a timing ts, when irradiation is initiated. In other words, the irradiation control means exerts control such that irradiation time IT=Tm·m=1.6·3=4.8 seconds. The bulb current I may be any value from the viewpoint of removing the influence of noise due to the scattered radiation removing means. However, it is preferable for the bulb current I to be controlled such that irradiation is performed at the exact mAs value which is necessary to obtain the radiation image P, that is, I=a/ (Tm·m)= 90/4.8=18.5 mA.

Note that a case has been described in which the above Formulas (1) and (2) are employed to control the irradiation end timing when obtaining the radiation image P. Formulas (1) and (2) may also be employed to control an irradiation end timing te0 when obtaining the reference image Pref.

The reference image Pref is obtained by irradiation radiation for an amount of irradiation time ITref, which is the amount of time for k periodic reciprocal motions of the scattered radiation removing means 20, and the radiation image P is obtained by irradiation radiation for an amount of irradiation time IT, which is the amount of time for m periodic reciprocal motions of the scattered radiation removing means 20, in the manner described above. Thereby, the generation of residual error irregularities can be suppressed, and shading correction and gain correction using the reference image Pref can be administered onto the radiation image P efficiently. That is, noise components (low frequency components), which are generated due to the scattered radiation removing means 20 that moves reciprocally at a constant speed, are substantially the same for integer multiples of a period of reciprocal motion, that is, k periodic reciprocal motions and m periodic reciprocal motions. Therefore, a single reference image Pref may be used to administer shading correction and gain correction onto a plurality of radiation images P, which are obtained by being irradiated with radiation for different amounts of time. Accordingly, the generation of residual error irregularities in the reference image Pref and radiation images P can be suppressed, and shading correction and the like can be administered efficiently.

Figure 7:
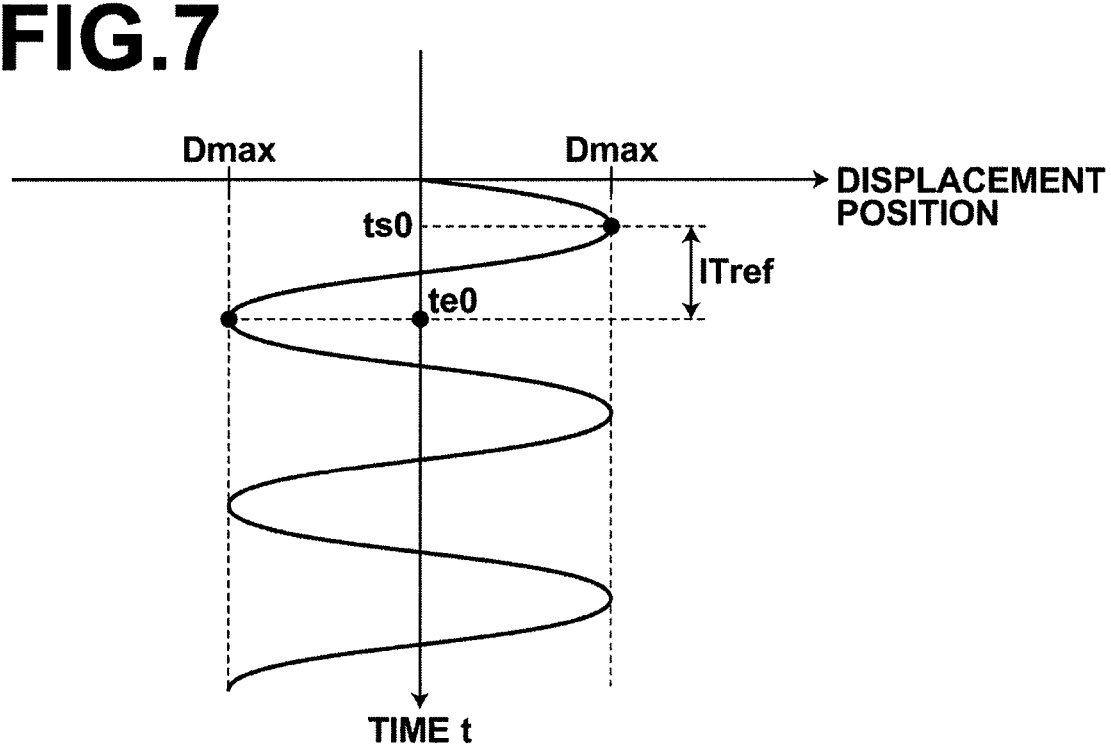
FIG. 7 is a graph that illustrates another example of the relationship between irradiation timings and movement of a scattered radiation removing means when the radiation image detecting apparatus of FIG. 4 obtains a reference image.
Figure 8:
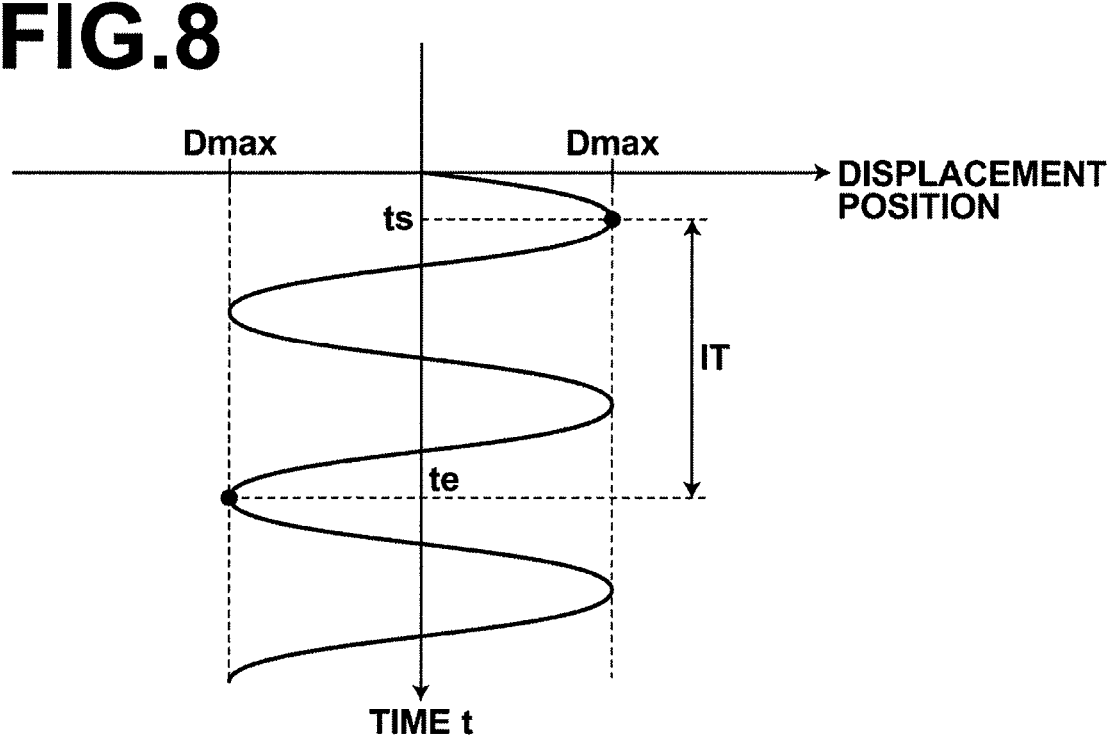
FIG. 8 is a graph that illustrates another example of the relationship between irradiation timings and movement of a scattered radiation removing means when the radiation image detecting apparatus of FIG. 4 obtains a radiation image.

FIG. 7 and FIG. 8 are graphs that illustrate a second embodiment of the irradiation timings employed by the radiation image detecting apparatus of the present invention. The irradiation timings which are employed when obtaining a reference image Pref and a radiation image P will be described with reference to FIG. 7 and FIG. 8. Note that the irradiation timings illustrated in FIG. 7 and FIG. 8 differ from the irradiation timings illustrated in FIG. 5 and FIG. 6 in that the irradiation timings are controlled using the maximally displaced positions Dmax of the scattered radiation removing means 20 as references.

Specifically, the irradiation control means 50 exerts control such that radiation is irradiated from the radiation source 2 at a timing ts0, at which the scattered radiation removing means 20 is at one of its two maximally displaced positions Dmax, when obtaining a reference image Pref, as illustrated in FIG. 7. If the scattered radiation removing means 20 is not positioned at a maximally displaced position Dmax, irradiation of radiation is not started until the scattered radiation removing means 20 moves to one of its two maximally displaced positions Dmax. The irradiation control means 50 exerts control such that the irradiation of radiation is ceased at a timing te0, which is an amount of time during which the scattered radiation removing means 20 has moved for p/2 periodic reciprocal motions (p is an integer greater than or equal to 1) after the initiation of the irradiation of radiation. Note that FIG. 7 illustrates an example in which a reference image Pref is obtained by irradiating radiation for an amount of time ITref that corresponds to half of a single periodic reciprocal motion (p=1).

Similarly, the irradiation control means 50 exerts control such that radiation is irradiated from the radiation source 2 at a timing ts, at which the scattered radiation removing means 20 is at one of its two maximally displaced positions Dmax, when obtaining a radiation image P, as illustrated in FIG. 8. In this case as well, if the scattered radiation removing means 20 is not positioned at a maximally displaced position Dmax, irradiation of radiation is not started until the scattered radiation removing means 20 moves to one of its two maximally displaced positions Dmax. The irradiation control means 50 exerts control such that the irradiation of radiation is ceased at a timing te, which is an amount of time during which the scattered radiation removing means 20 has moved for q/2 periodic reciprocal motions (q is an integer greater than or equal to 1) after the initiation of the irradiation of radiation.

Note that FIG. 8 illustrates an example in which a radiation image P is obtained by irradiating radiation for an amount of time IT that corresponds to one and a half (3/2) periodic reciprocal motions (q=3).

As can be understood from the above description, the maximally displaced positions refer to both the rightmost position Dmax and the leftmost position Dmax. For example, irradiation may be initiated at a timing when the scattered radiation removing means 20 is positioned at the rightmost Dmax when obtaining the reference image Pref, and irradiation may be initiated at a timing when the scattered radiation removing means 20 is positioned at the leftmost Dmax when obtaining radiation images P.

Here, the amount of irradiation time (the integer q) when obtaining the radiation image P may be determined by operator input to the irradiation control means 50. Alternatively, the amount of irradiation time may be determined in the following manner. When an mAs value of radiation necessary to obtain a radiation image P is specified, the irradiation control means 50 calculates the value of the integer q according to the following two formulas (3) and (4):

$$q = \text{the smallest integer not less than a value } r \quad (3)$$

$$r = a/(I_{max} \cdot tm) \quad (4)$$

wherein Imax is the maximum bulb current of the radiation source, tm is the amount of time for the scattered radiation removing means to move one way in the reciprocal motion thereof, and a is the mAs value of radiation.

In the case that the number r calculated by Formula (4) includes decimal places, the decimal places are rounded up, then the value of the integer q is calculated (by Formula (1)). For example, consider a case that the maximum bulb current Imax of the radiation source 2 is 20 mA, and the amount of time tm for the scattered radiation removing means 20 to move one way in the reciprocal motion thereof is 0.8 seconds. In this case, if a radiation image P is to be obtained with an mAs value of a=90 mAs, the irradiation control means 50 calculates r=a/(Imax·Tm)=5.625, and derives r=6 by rounding up the decimal places. Accordingly, the irradiation control means 50 exerts control such that irradiation is ceased at a timing te, which is after three periodic reciprocal motions (q=6) from a timing ts, when irradiation is initiated. In other words, the irradiation control means exerts control such that irradiation time IT=tm·q=0.8·6=4.8 seconds. The bulb current I may be any value from the viewpoint of removing the influence of noise due to the scattered radiation removing means. However, it is preferable for the bulb current I to be controlled such that irradiation is performed at the exact mAs value which is necessary to obtain the radiation image P, that is, I=a/(tm·q)=90/4.8=18.5 mA.

Note that a case has been described in which the above Formulas (3) and (4) are employed to control the irradiation end timing when obtaining the radiation image P. Formulas (3) and (4) may also be employed to control an irradiation end timing te0 when obtaining the reference image Pref.

In this case as well, the noise components that appear in the reference image Pref due to the scattered radiation removing means 20 and the noise components that appear in radiation images P due to the scattered radiation removing means 20 are substantially the same. Therefore, residual error irregularities that occur after shading correction or the like can be suppressed, and the image processing apparatus 100 is enabled to efficiently administer shading correction and gain correction.

According to the embodiments described above, the radiation image detecting apparatus 1 is equipped with: the radiation source 2 for irradiating radiation; the radiation detector 10 for detecting radiation, which is irradiated by the radiation source 2 onto a subject and which has passed through the subject, as a radiation image; the scattered radiation removing means 20 for removing scattered components of the radiation, provided on the radiation detector 10 toward the side onto which the radiation is irradiated; the reciprocal drive means 30, for reciprocally moving the scattered radiation removing means 20 with respect to the radiation detector 10; the position detecting means 40, for detecting the position of the scattered radiation removing means 20 with respect to the radiation detector 10 from the reciprocal driving means 30; and the irradiation control means 50, for controlling the irradiation of radiation onto the radiation detector 10. The irradiation control means controls the amounts of time that radiation is irradiated and irradiation timings during obtainment of radiation images P, which are obtained by the radiation detector 10 detecting radiation which has passed through subjects, and during obtainment of the reference image Pref, which is employed to correct the radiation images P, based on the position of the scattered radiation removing means 20 detected by the position detecting means 40. The irradiation control means 50 controls irradiation of the radiation during obtainment of the reference image Pref such that the irradiation is ceased after the scattered radiation removing means 20 is reciprocally moved for k periodic reciprocal motions (k is an integer greater than or equal to 1) from initiation of the irradiation, and controls irradiation of the radiation during obtainment of the radiation images P such that the irradiation is ceased after the scattered radiation removing means is reciprocally moved for m periodic reciprocal motions (m is an integer greater than or equal to 1). In cases that the amount of time ITref that radiation is irradiated when obtaining a reference image Pref and the amounts of time IT that radiation is irradiated when obtaining radiation images are integer multiples of half the periods of reciprocal motion of the scattered radiation removing means 20, noise components which are included in the reference image Pref and the radiation images P are substantially the same. Therefore, if a single reference image Pref is obtained, the reference image Pref may be used to correct radiation images P which are obtained by being irradiated with radiation for different amounts of time. Accordingly, residual error irregularities can be reduced, and radiation images can be corrected efficiently.

In addition, the irradiation control means 50 controls irradiation of the radiation during obtainment of the reference image Pref such that the irradiation is initiated when the scattered radiation removing means 20 is at its maximally displaced position within the reciprocal motion thereof, and is ceased when the scattered radiation removing means 20 is reciprocally moved for p/2 periodic reciprocal motions (p is an integer greater than or equal to 1), and controls irradiation of the radiation during obtainment of radiation images P such that the irradiation is initiated when the scattered radiation removing means 20 is at its maximally displaced position within the reciprocal motion thereof, and is ceased when the scattered radiation removing means 20 is reciprocally moved for q/2 periodic reciprocal motions (p is an integer greater than or equal to 1), as illustrated in FIG. 7 and FIG. 8. In cases that the amount of time ITref that radiation is irradiated when obtaining a reference image Pref and the amounts of time IT that radiation is irradiated when obtaining radiation images are integer multiples of half the periods of reciprocal motion of the scattered radiation removing means 20, noise components which are included in the reference image Pref and the radiation images P are substantially the same. Therefore, if a single reference image Pref is obtained, the reference image Pref may be used to correct radiation images P which are obtained by being irradiated with radiation for different amounts of time. Accordingly, residual error irregularities can be reduced, and radiation images can be corrected efficiently.

The present invention is not limited to the embodiments described above. For example, the above embodiments are described as cases in which the radiation images are images obtained by a mammography apparatus. Alternatively, the radiation images may be those obtained by imaging the chests of subjects. Further, the radiation images are not limited to those for medical use, and may also include radiation images which are employed for non destructive inspections.

In addition, the image processing apparatus 100 may function to administer a trimming process that trims the regions within radiation images P corresponding to the maximally displaced positions Dmax, in addition to the shading correction and the gain correction. The trimming process may be administered, because the regions corresponding to the maximally displaced positions Dmax are regions at which the scattered radiation removing means 20 is static, which may lead to cases in which stripes are generated due to the scattered radiation removing means 20.

Further, the above embodiments are described as cases in which the reference image Pref is obtained first, then the radiation image P is obtained. However, radiation images P may be obtained first, and then the reference image Pref for correcting the radiation images P may be obtained.

What is claimed is:

1. A radiation image detecting apparatus, comprising:
   a radiation source for irradiating radiation;
   a radiation detector for detecting radiation, which is irradiated by the radiation source onto a subject and which has passed through the subject, as a radiation image;
   scattered radiation removing means for removing scattered components of the radiation, provided on the radiation detector toward the side onto which the radiation is irradiated;
   reciprocal drive means, for reciprocally moving the scattered radiation removing means in one of a main direction and a sub direction of the radiation detector;
   image correcting means, for correcting the radiation image which is obtained by the radiation detector by detecting the radiation which has passed through the subject with a reference image; and
   irradiation control means, for controlling the irradiation of radiation onto the radiation detector;
   the irradiation control means controlling irradiation of the radiation during obtainment of the reference image such that the irradiation is ceased after the scattered radiation removing means is reciprocally moved for k periodic reciprocal motions (k is an integer greater than or equal to 1) from initiation of the irradiation, and controlling irradiation of the radiation during obtainment of the radiation image such that the irradiation is ceased after the scattered radiation removing means is reciprocally moved for m periodic reciprocal motions (m is an integer greater than or equal to 1).

2. A radiation image detecting apparatus as defined in claim 1, wherein:
   the irradiation control means sets the value of m to be the smallest integer which is not less than a value n (n=a/(Imax·Tm), wherein Imax is the maximum bulb current of the radiation source, Tm is the amount of time for reciprocal motion of the scattered radiation removing means, and a is the mAs value of radiation).

3. A radiation image detecting apparatus as defined in claim 1, wherein:
the image correcting means employs the reference image to administer gain correction on the radiation image.

4. A radiation image detecting apparatus, comprising:
a radiation source for irradiating radiation;
a radiation detector for detecting radiation, which is irradiated by the radiation source onto a subject and which has passed through the subject, as a radiation image;
scattered radiation removing means for removing scattered components of the radiation, provided on the radiation detector toward the side onto which the radiation is irradiated;
reciprocal drive means, for reciprocally moving the scattered radiation removing means in one of a main direction and a sub direction of the radiation detector;
position detecting means, for detecting the position of the scattered radiation removing means with respect to the radiation detector;
image correcting means, for correcting the radiation image which is obtained by the radiation detector by detecting the radiation which has passed through the subject with a reference image; and
irradiation control means, for controlling the timing of irradiation of radiation onto the radiation detector based on the position of the scattered radiation removing means detected by the position detecting means when obtaining the radiation image and the reference image;
the irradiation control means controlling irradiation of the radiation during obtainment of the reference image such that the irradiation is initiated when the scattered radiation removing means is at its maximally displaced position within the reciprocal motion thereof, and is ceased when the scattered radiation removing means is reciprocally moved for p/2 periodic reciprocal motions (p is an integer greater than or equal to 1), and controlling irradiation of the radiation during obtainment of the radiation image such that the irradiation is initiated when the scattered radiation removing means is at its maximally displaced position within the reciprocal motion thereof, and is ceased when the scattered radiation removing means is reciprocally moved for q/2 periodic reciprocal motions (q is an integer greater than or equal to 1).

5. A radiation image detecting apparatus as defined in claim 4, wherein:
the irradiation control means sets the value of q to be the smallest integer which is not less than a value r ($r=a/(Imax \cdot tm)$, wherein Imax is the maximum bulb current of the radiation source, tm is the amount of time for the scattered radiation removing means to move one way in the reciprocal motion thereof, and a is the mAs value of radiation).

6. A radiation image detecting apparatus as defined in claim 4, wherein:
the image correcting means employs the reference image to administer gain correction on the radiation image.

* * * * *